United States Patent [19]
Hetzel et al.

[11] Patent Number: 5,609,735
[45] Date of Patent: Mar. 11, 1997

[54] PROCESS AND A DEVICE FOR SEPARATING A SOLID RESIDUE FROM ITS SOLUTION IN A STIRRED BED OF MATERIAL

[75] Inventors: Hartmut Hetzel, Köln; Dieter Grenner, Leverkusen; Wolfgang Ebner, Dormagen; Klaus Biskup, Leverkusen, all of Germany

[73] Assignee: Bayer Aktiengesellschaft, Leverkusen, Germany

[21] Appl. No.: 518,092

[22] Filed: Aug. 22, 1995

[30] Foreign Application Priority Data

Aug. 31, 1994 [DE] Germany .................... 44 30 951.1

[51] Int. Cl.⁶ .................................................. B01D 3/34
[52] U.S. Cl. .................... 203/52; 203/91; 203/DIG. 25; 202/182; 202/226
[58] Field of Search ........................... 203/52, DIG. 25, 203/91; 202/152, 182, 226, 238; 560/352

[56] References Cited

U.S. PATENT DOCUMENTS

| 2,889,257 | 6/1959 | Griffin et al. | 202/52 |
| 3,140,305 | 7/1964 | Lowenstein | 260/453 |
| 3,687,422 | 8/1972 | List | 59/104 |
| 4,216,063 | 8/1980 | Ailloud et al. | 203/91 |
| 4,913,771 | 4/1990 | McIntyre | 159/47.1 |
| 5,183,540 | 2/1993 | Rubin | 203/41 |
| 5,349,082 | 9/1994 | Slack et al. | 560/352 |
| 5,354,432 | 10/1994 | Arribas et al. | 203/68 |
| 5,446,196 | 8/1995 | Benedix et al. | 560/352 |

FOREIGN PATENT DOCUMENTS 3215577  10/1983  Germany .

Primary Examiner—Christopher Kim
Attorney, Agent, or Firm—Joseph C. Gil; Noland J. Cheung

[57] ABSTRACT

A process and a device are described for separating a solid residue, after separation, from a solution of the residue in evaporable materials and/or solvents with the addition of up to 20% by weight of high-boiling hydrocarbons that are inert under evaporation conditions of the evaporable materials, heating the mixture to evaporation temperature under vacuum, whereby the evaporable materials evaporate, are drawn off and condensed, and the residue is obtained as a free-flowing solid, the residue solution being introduced onto a stirred bed of granular solid material kept at the evaporation temperature.

7 Claims, 2 Drawing Sheets

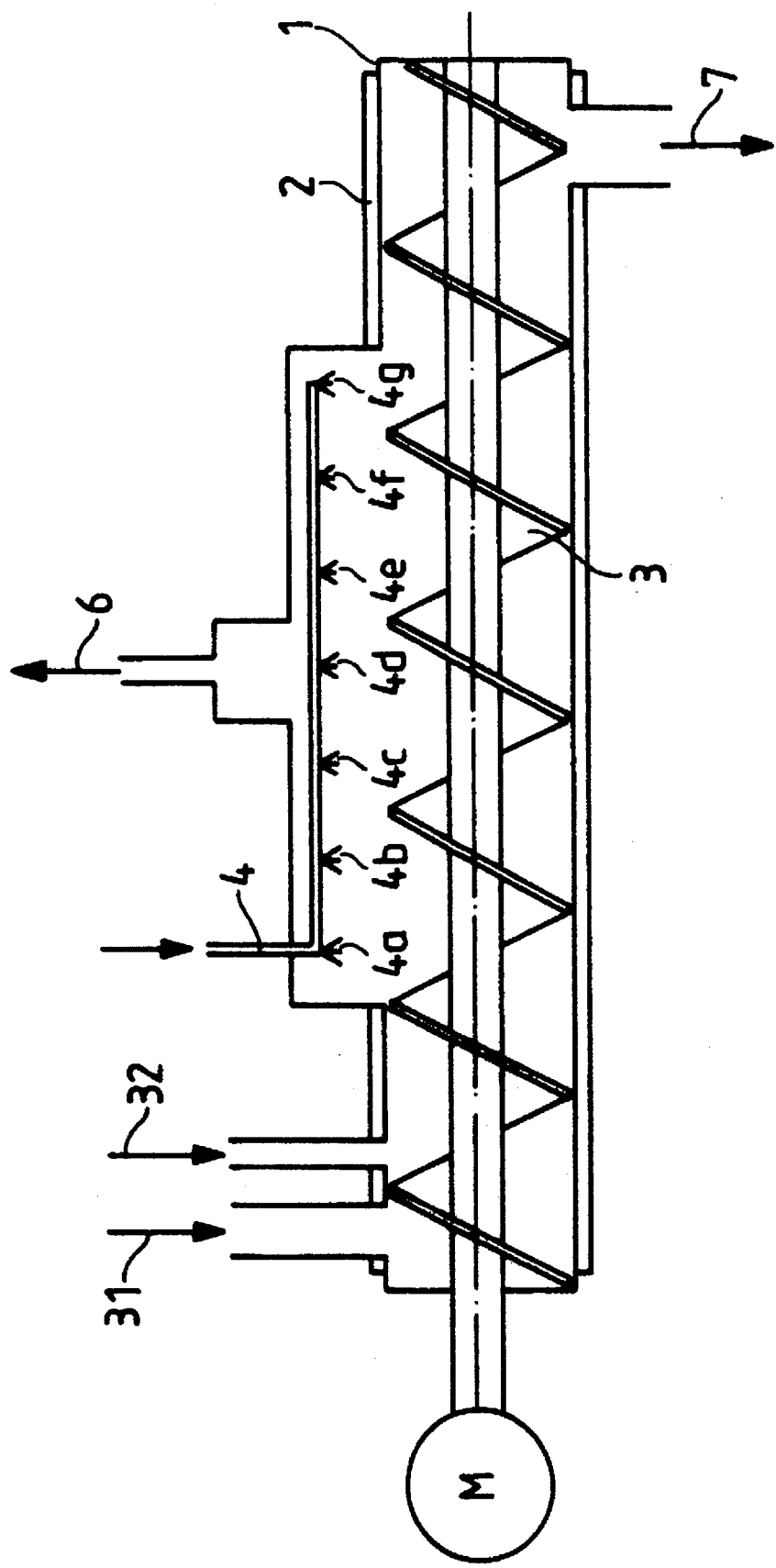

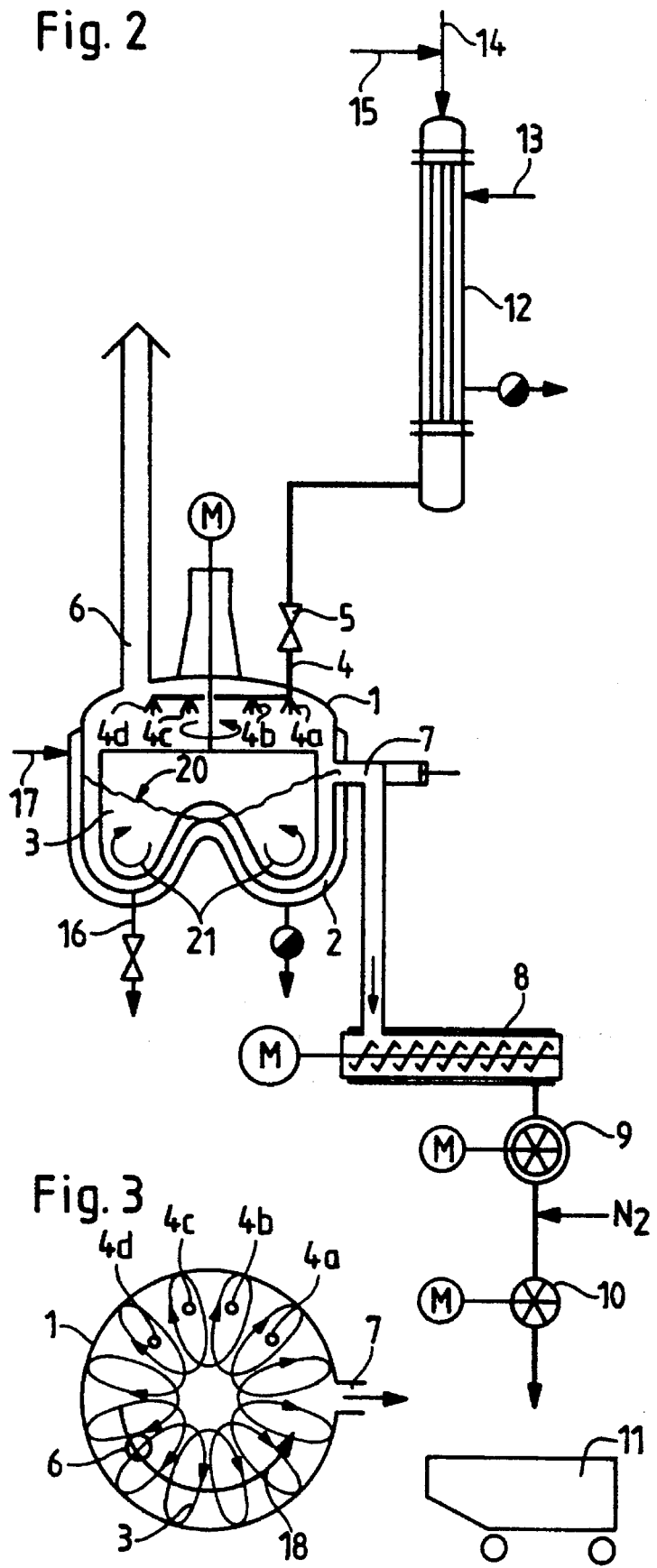

PROCESS AND A DEVICE FOR SEPARATING A SOLID RESIDUE FROM ITS SOLUTION IN A STIRRED BED OF MATERIAL

BACKGROUND OF THE INVENTION

In many separation processes, and in distillation processes in particular, essentially undefined solid residues are obtained after isolation as a bottom product, which have to be removed. In the interests of ease of handling, these solid residues are not isolated completely during distillation, but are expelled from the distillation process in the form of a solution in materials still capable of evaporation, or in specially added solvents. The residue solution requires further work-up in order to obtain the evaporable materials and to recover any solvents used. Work-up is generally carried out in such a way that the residue solution is heated to the evaporation temperature for the evaporable materials and solvents. The evaporating substances are drawn off and a solid, free-flowing residue is obtained which is conveyed to a further disposal operation such as incineration or dumping. A problem from the process technology angle is that while the evaporable materials or solvents are being evaporated, the residue solution changes from a liquid state via a state with a viscous, sticky consistency to the solid residue. If evaporation takes place batchwise in stirred apparatus, the transition may be observed on the basis of the greatly increasing stirrer power required during the passage through the viscous-sticky state. During the viscous-sticky state, moreover, the heat transfer to the residue mass (introduction of the heat of evaporation) and the mixing required to produce new surfaces with a high concentration of evaporable substances is greatly impeded.

An example of such distillation residues are residues from distillation during the production of isocyanates, particularly toluene diisocyanate (TDI), a chief component for the production of polyurethanes. The production of isocyanates takes place by phosgenation of corresponding amines, the reactants being reacted in a solvent, usually ortho-dichlorobenzene. The reaction takes place with a yield of approx. 96 to 98%, with primarily isocyanate polymers being formed as by-products.

In order to obtain pure isocyanates, the crude isocyanate solution obtained by phosgenation is distilled in several partial stages. A residue solution which, in the case of TDI production, contains about 5 to 20% of polymeric TDI, is obtained as a bottom product of the distillation columns. Evaporable proportions of TDI and solvents have to be evaporated from the residue solution to obtain a solid, free-flowing residue.

According to U.S. Pat. No. 2,889,257, it has already been proposed to work up residue solutions from isocyanate production by introducing the residue solution into a stirred vessel containing inert, high-boiling hydrocarbons at a temperature of 200° to 350° C., the evaporable proportions of the residue solution evaporating and being drawn off, and solid residue particles being formed in the hot hydrocarbon oil. The hot hydrocarbon oil is pumped around between the stirred vessel and a heat exchanger, the solid particles being expelled by gravimetry from a partial stream. As a result of this inherently complex process, the transition via the viscous-sticky state of the residue solution is avoided, but the process requires elaborate apparatus and, in addition, requires the work-up of the hydrocarbon oil at certain intervals.

According to a more recent proposal in European Patent 548,685, work-up takes place batchwise in a stirred vessel in which is placed a charge of 5 to 20% of bitumen based on the quantity of residue solution at a temperature of 150° to 280° C., to which the residue solution is then introduced continuously, the evaporable constituents of the residue solution being drawn off at a pressure of 2 to 30 mbar. When the charge has ended, a solid residue is obtained in the form of a crumbly, free-flowing mass. The bitumen charge evidently fulfills the several functions. The stirred vessel is initially provided with a sufficient heat capacity to evaporate the evaporable constituents of the residue solution, so that temperature variations are avoided. During the initial introduction of residue solution, the bitumen ensures a rapid distribution of the residue solution in the stirred vessel. Caking of solid residue on the stirrer and container walls is avoided. Moreover, the formation of small residue crumbs is promoted. However, the problem of the transition via the viscous-sticky state, which requires a substantially increased stirring power, is only slightly reduced. Moreover, a disadvantage is the batchwise mode of operation requiring large numbers of operatives, which mode can be designed as a quasi continuous operation only by the alternating operation of several stirred vessels.

BRIEF DESCRIPTION OF THE DRAWINGS

FIG. 1 illustrates a screw drier suitable for use in the present invention.

FIG. 2 represents a schematic of a process and apparatus according to the present invention.

FIG. 3 is a top view of a stirred bed for use in the present invention.

DESCRIPTION OF THE INVENTION

According to the invention, it is now proposed that the residue solution, optionally after mixing with up to 20% by weight of bitumen based on the weight of the residue solution, be introduced onto a stirred bed of solid, granular material which is kept at the temperature required for the evaporation of the evaporable materials and/or solvents.

The object of the present invention is, therefore, a process for separating a solid residue, after separation, from a solution of the residue in evaporable materials and/or solvents, optionally with the addition of up to 20% by wt. of high-boiling hydrocarbons, which are inert under the evaporation conditions of the evaporable materials, heating the mixture to evaporation temperature under vacuum, whereby the evaporable materials evaporate, are drawn off and condensed, and whereby the residue is obtained as a free-flowing solid, characterized in that the residue solution is introduced onto a stirred bed of free-flowing solid material kept at the evaporation temperature.

Preferably, solid residue that was obtained during a prior separation is used as the free-flowing solid material. However, other material such as sand, gravel, pumice, slack or other may also be used as the free-flowing solid material.

Preferably, the distillation bottom product from the distillation operation of isocyanate production, particularly TDI production, is used as residue solution.

The high-boiling inert hydrocarbon used is preferably bitumen, in connection with the work-up of isocyanate distillation residues, particularly preferably in a quantity of 1 to 10% by weight, and more preferably in a quantity of 1 to 5% by weight, based on the quantity of residue solution.

The process is not, however, restricted to the work-up of the distillation bottom product from isocyanate production, but is generally suitable for the work-up of solutions or suspensions by separation of evaporable constituents to produce a solid residue. Examples of fields of application for the process according to the invention are the work-up of distillation residues in general, of ceramic suspensions, of pigment suspensions, or of whey emulsions obtained during cheese production. The solid obtained as residue may also be a valuable substance of primary interest to be recovered, e.g. following extraction processes.

Without restricting the generality of the invention, it will be described on the basis of the work-up of the distillation bottom product of isocyanate production as an example.

The process according to the invention may be carried out batchwise or continuously. In batchwise operation, the charge of free-flowing solid material is placed in a vessel provided with a stirrer, the vessel is brought to the evaporation temperature of the evaporable substances and evacuated. After the operating conditions for the separation have been reached, the residue solution is introduced into the vessel, the evaporable substances being drawn off via the gas phase. The residue solution is introduced at such a rate that the mean bed temperature remains constant, i.e. it does not fall and the power consumption of the stirrer does not increase.

The bed is preferably stirred in a wall-sweeping operation so that a good heat transfer between the heated vessel wall and the bed is ensured and a complete circulation of the solid, free-flowing material takes place, if possible, in the entire stirred vessel in order to guarantee an even heat distribution in the vessel, if possible. "Wall-sweeping" in this case means that the stirrer has a gap from the wall of the vessel of 2 to 20 min.

When the residue solution is introduced onto the stirred solid bed, the residue solution is distributed to such an extent that the evaporable constituents evaporate spontaneously at the prevailing temperature and the pressure of preferably 2 to 30 mbar, and more preferably 10 to 20 mbar, the transition via the viscous-sticky state taking place in such thin films that the properties of the bed are not affected. If residue solutions from TDI distillation are being worked up, the stirred bed preferably has a temperature of 150° to 280° C., and more preferably 180° to 230° C.

While the residue solution is being introduced, solid residue is formed continuously, so that the mass of the bed is increased until the capacity of the vessel is reached. The vessel is then emptied to such an extent that only as much solid remains in the vessel as is required as a charge for the bed of the next charge.

The quantity of free-flowing solid material placed in the stirred vessel, i.e. the quantity of solid residue remaining in the vessel after emptying, is preferably at least 10%, and more preferably 15 to 30% of the vessel capacity.

Preferably, the process according to the invention is carried out continuously. The continuous process may be carried out in a heated, axially conveying screw drier or paddle drier with a degassing facility. At the entrance of the screw drier, the solid granular material forming the bed is introduced continuously, according to the invention. The residue solution is metered in continuously at an interval in the direction of conveyance of the screw drier that is sufficient to heat the granular material to evaporation temperature. The solid residue formed is expelled continuously at the outlet end of the screw drier.

In order to keep down the required quantity of solid granular material (bed charge) to be introduced into the screw drier without a liquid phase forming at the feed point for the residue solution in the screw drier, the feed of residue solution is preferably distributed over the length of the screw drier. The quantity of granular material required and introduced may thus be kept at 10 to 30% by weight of the screw output.

Preferably, the continuous process is carried out in a stirred vessel, the stirrer taking the form of wall-sweeping agitator blades dividing up the vessel into radial segments, so that a circulatory movement of the material is ensured. The residue solution is introduced outside the vessel axis. The solid residue is expelled at the radius of the vessel at a point which is as far as possible from the inlet point for the residue solution, in the direction of rotation of the stirrer. Preferably, the residue solution is introduced via several inlet points arranged concentrically to the stirrer axis.

An agitator blade dividing the cross-section of the vessel radially is preferably composed of a large number of smaller, inclined agitator blades that overlap each other.

Preferably, the bed is stirred such that the residue particles in general describe an approximately toroidal path. In the case of stirrer blades adjusted to the cross-section of the stirred vessel, such a toroidal path is promoted by the fact that the base of the stirred vessel takes the form of a dished end. Most preferably, the dished end of the stirred vessel tapers towards the middle, so that the stirred vessel takes the form of a circular trough.

The continuous removal of the solid residue and the introduction of the residue solution onto the bed takes place preferably successively in the sequence mentioned in relation to the direction of rotation of the stirrer, and adjacently so that the particles of the material bed migrate from the point of introduction of the residue solution through the preferably circular trough-shaped vessel until removal of the solid residue spirally in the direction of rotation of the stirrer. In this way, the residue particles attain a defined minimum residence time in the stirred vessel after they have come into contact with the residue solution.

The object of the present invention is also a device for carrying out the process, containing a heated stirred vessel with a wall-sweeping stirrer, means for maintaining reduced pressure in the vessel, means for the continuous introduction of residue solution into the vessel, and means for removing free-flowing solid residue from the vessel. Preferably, the stirred vessel has a dished end, and, most preferably, the stirred vessel takes the form of a circular trough.

Further details of the present invention are explained on the basis of the drawings, which show a particularly preferred embodiment of the present invention.

FIG. 1 shows a screw drier suitable for the process according to the invention. The screw housing 1 has a heating jacket 2 and a wall-sweeping screw element or paddles 3. Arrow 31 designates the point of introduction for the granular material. Moreover, an inlet 32 for bitumen may be provided. The residue solution is introduced via line 4 with inlet nozzles 4a to 4g. Evaporated valuable materials are removed by suction along arrow 6. The solid residue is removed at 7.

FIG. 2 shows a circular trough-shaped stirred vessel 1 with heating jacket 2 and wall-sweeping stirrer 3. The bed of solid residue particles, whose surface is indicated 20, executes the circular movements indicated by arrows 21 under the rotational movement of the stirrer vertically to the movement of stirrer 3. Residue solution is introduced via valve 5 and line 4, and sprayed onto the material via nozzles 4a to 4d. The evaporating solvents and valuable materials are drawn off via line 6 by means of a vacuum pump, conveyed to a condenser, not shown, and then distilled. Continuously formed solid residue is removed to container 11 via the outlet 7 by way of vacuum lock 9 after cooling in cooling coil 8. If necessary, a second lock 10 is provided, in which case nitrogen may be introduced between locks 9 and 10 so that the passage of atmospheric oxygen into stirred vessel 1 is excluded. A falling film evaporator 12 with a heating medium supply 13 may be installed upstream of the introduction of the residue solution into the stirred vessel, into which evaporator the residue solution is introduced via line 14, bitumen being added optionally via line 15. The falling film evaporator is installed in particular if residue solutions with a solid residue content, after separation, of less than 40% by weight are used, since the capacity of the stirred vessel may thereby be increased considerably.

FIG. 3 shows a top view of the stirred bed to explain the toroidal paths of movement 21 of the toroid particles. The outlet 7 for the residue to be expelled is arranged adjacent to and behind the inlet 4 for the residue solution in relation to the direction of rotation 18 of the stirrer.

What is claimed is:

1. In a process for separating a solid residue from a solution of the residue in evaporable materials and/or solvents with the addition of up to 20% by weight of high-boiling hydrocarbons which are inert under evaporation conditions of the evaporable materials comprising heating said solution under vacuum to the evaporation temperature of said evaporable materials, whereby said evaporable materials evaporate, are drawn off and condensed and whereby the residue is obtained as a free-flowing solid, the improvement wherein said solution is introduced onto a stirred bed of granular, solid material kept at said evaporation temperature.

2. The process of claim 1, wherein free-flowing solid residue is removed continuously from the stirred bed.

3. The process of claim 1, wherein said granular solid material comprises said free-flowing solid.

4. The process of claim 1, wherein said granular, solid material is introduced into a heated, axially conveying screw provided with a suction means to remove evaporated material, and said solution is introduced onto said granular, solid material being conveyed.

5. The process of claim 1, wherein said granular, solid material is introduced into a paddle drier provided with a suction means to remove evaporated material, and said solution is introduced onto said granular, solid material in said drier.

6. The process of claim 1, wherein said solution is introduced continuously into a stirred vessel containing said granular, solid material.

7. The process of claim 1, wherein a distillation bottom product from the production of toluene diisocyanate is used as said solution.

\* \* \* \* \*